United States Patent [19]

Lennox

[11] Patent Number: 5,575,772
[45] Date of Patent: Nov. 19, 1996

[54] ALBATION CATHETERS

[75] Inventor: Charles D. Lennox, Hudson, N.H.

[73] Assignee: Boston Scientific Corporation, Natick, Mass.

[21] Appl. No.: 601,834

[22] Filed: Feb. 15, 1996

Related U.S. Application Data

[63] Continuation of Ser. No. 86,740, Jul. 1, 1993, abandoned.

[51] Int. Cl.⁶ .................................................. A61M 25/00
[52] U.S. Cl. ................................................................ 604/96
[58] Field of Search .............................. 604/20, 49, 52, 604/53, 96–103, 113, 114; 606/28, 31, 41, 194

[56] References Cited

U.S. PATENT DOCUMENTS

| | | | |
|---|---|---|---|
| 3,995,623 | 12/1976 | Blake et al. | 128/2.06 E |
| 4,407,294 | 10/1983 | Vilkomerson | 128/660 |
| 4,641,649 | 2/1987 | Walinsky et al. | 128/303.1 |
| 4,676,258 | 6/1987 | Inokuchi et al. | 128/804 |
| 4,709,698 | 12/1987 | Johnston et al. | |
| 4,821,731 | 4/1989 | Martinelli et al. | 128/662.06 |
| 4,841,977 | 6/1989 | Griffith et al. | 128/660.03 |
| 4,951,677 | 8/1990 | Crowley et al. | 128/662.06 |
| 4,955,377 | 9/1990 | Lennox et al. | |
| 4,998,933 | 3/1991 | Eggers et al. | 606/41 |
| 5,000,185 | 3/1991 | Yock | 128/662.03 |
| 5,054,492 | 10/1991 | Scribner et al. | 128/662.06 |
| 5,103,804 | 4/1992 | Abele et al. | |
| 5,106,360 | 4/1992 | Ishiware et al. | 600/2 |
| 5,131,397 | 7/1992 | Crowley | 128/662.06 |
| 5,140,987 | 8/1992 | Schuger et al. | 128/642 |
| 5,156,151 | 10/1992 | Imran | |
| 5,190,540 | 3/1993 | Lee | 606/28 |
| 5,222,501 | 6/1993 | Ideker et al. | 128/660.03 |
| 5,226,430 | 7/1993 | Spears et al. | 128/898 |
| 5,325,860 | 7/1994 | Seward et al. | 128/662.06 |
| 5,336,222 | 8/1994 | Durgin, Jr. et al. | 606/50 |
| 5,403,311 | 4/1995 | Abele et al. | 606/49 |

FOREIGN PATENT DOCUMENTS

WO92/03095 3/1992 WIPO .............................. A61B 8/12

OTHER PUBLICATIONS

U.S. Ser. No. 08/038,903 Electro–Coagulation, Ablation and Other Electrotherapeutic Treatments of Body Tissue, filed Mar. 29, 1993, Abele et al.
U.S. Ser. No. 07/957,533 Device and Method for Heating tissue in a Patient's body, filed Oct. 15, 1992, Fram et al.
Polaris Series Steerable/Deflectable Tip Mapping Catheters brochure, Mansfield Boston Scientific Corporation.

(List continued on next page.)

*Primary Examiner*—Manual Mendez
*Attorney, Agent, or Firm*—Fish & Richardson P.C.

[57] ABSTRACT

A balloon catheter is provided that includes a catheter shaft constructed for insertion into a blood vessel, an inflatable balloon mounted on a distal portion of the catheter shaft, a heating device mounted on the distal portion of the catheter arranged for heating tissue in contact with the balloon while the balloon is inflated, and an ablation electrode. The catheter shaft and the balloon are sized and constructed to permit the distal portion of the catheter shaft to be inserted into an atrium or ventricle of a heart while the balloon is deflated. The distal portion of the catheter is positioned within the atrium or ventricle and adjacent to a wall of the atrium or ventricle. The balloon is inflated with fluid while the balloon is within the atrium or ventricle, and while the balloon is inflated it is engaged in direct contact with a wall of the atrium or ventricle. Tissue surrounding the balloon is heated through use of the heating device while the balloon is inflated. In one embodiment the balloon disposed is annularly around a distal tip of the catheter shaft, and the electrode is located on the distal tip of the catheter for directly contacting tissue while the balloon is pressed against the tissue in an axial direction. In other embodiments, a suction port is located at the distal tip of the catheter, and a tissue-engagement device surrounds the distal port and is constructed to engage tissue with suction when the port is placed adjacent to the tissue.

35 Claims, 7 Drawing Sheets

OTHER PUBLICATIONS

Explorer Series Electrophysiology Mapping Catheters brochure, Mansfield Boston Scientific Corporation.

Explorer 360° Series Advanced Electrophysiology Mapping Catheters brochure, Mansfield Boston Scientific Corporation.

Gold Probe—The Next Generation on Bipolar Hemostasis brochure, Microvasive Boston Scientific Corporation.

Advanced Materials & Processes Surface Engineering, ASM International, Dec. 1990 vol. 138 Issue 6.

Anatomy and Physiology brochure, Mansfield Boston Scientific.

Frank et al., Implantable cardioverter–defibrillators: alternative treatment for ventricular tachyarrhythmias, Mar. 1992, vol. 3., No. 3, Coronary Artery Disease, 1992 Current Science ISSN 0954–6928.

Becker et al., Radiofrequency Baloon Angioplasty Rationale and Proof of Principle, Nov. 1988, Investigative Radiology, vol. 23, pp. 810–817.

Critelli, Transcatheter Aglation of Tachyarrhythmias: An Evolving Therapeutic Procedure, 1989, Journal of Interventional Cardiology, vol. 2, No. 4, pp. 233–236.

Buxton, Catheter Ablation of Atrioventricular Bypass Tracts Still an Investigational Procedure, Jun. 1989 Circulation, vol.79, No. 6, pp. 1388–1390.

Borggrefe et al., Electophysiology, Pacing, and Arrhythmia, Catheter Ablation Using Radiofrequency Energy. Feb. 1990, Clin. Cardio. 13, 127–131.

Avitall et al., The Physics and Engineering of Transcatheter Cardiac Tissue Ablation, University of Wisconsin–Milwaukee Clinical Campus.

Interventional Electrophysiology Poised for Growth, Sep. 12, 1991, The BBI Newsletter, vol. 14, No. 9 pp. 162–165.

McGuire et al., Surgical techniquest for the cure of atrioventricular junctional reentrant tachycardia, Mar. 1992, Coronary Artery Disease, vol. 3, No. 3. pp. 186–191.

Selle, Definitive surgery for postinfarction ventricular tachycardia, Mar. 1992, Coronary Artery Disease, vol. 3, No. 3, pp. 204–209.

Mahomed et al., Surgery for Wolff–Parkinson–White syndrome, 1992 Current Science ISSN 0954–6928, pp. 175–185.

Sung, Arrhythmias and the Autonomic Nervous System, Sept. 1987, Cardio, pp. 77–80.

The Soft Steerable Catheter System for Rapid GI Intubation and Decompression and Sampling, Oct. 1978 Medi Tech Division Cooper Scientific Corporation.

Becker et al., Original Investigations: Radiofrequency Baloon Angioplasty Rationale and Proof of Principle, Nov. 1988 Investigative Radiology, vol. 23, pp. 810–817.

Tarjan et al., An experimental Device for Low–Energy, Precise Ablation of AV Conduction, Nov.–Dec. 1986, PACE vol. 9, pp. 1396–1402.

Saksena et al., Low–energy transvenous ablation of the canine atriobentricular conduction system with a suction electrode catheter, Aug. 1987, Circulation, vol. 76, No. 2, pp. 394–403.

Berns et al., "Feasibility of Radiofrequency–Powered, Thermal Balloon Ablation of Atrioventricular Bypass Tracts Via the Coronary Sinus"; Nov. 11–14, 1991, Anaheim Convention Center, Anaheim CA.

Calkins et al., "Diagnosis and Cure of the Wolff–Parkinson–White Syncrome or Paroxysmal Supraventricular Tachycardias During A Single Electrophysiologic Test"; *N.E. Journal of Med.*, vol. 324, No. 23, Jun. 6, 1991.

Crowley et al., "Optimized Ultrasound Imaging Catheters for Use in the Vascular System"; *International Journal of Cardiac Imaging* 4:145–141, 1989.

Crowley et al., "Ultrasound Guided Therapeutic Catheters: Recent Developments and Clinical Results"; *International Journal of Cardiac Imaging,* 6:145–156, 1991.

Ellis et al., "Ultrasonic Imaging Catheter"; Microvasive, Inc.; 1988.

Jackman et al., "Catheter Ablation of Accessory Atrioventricular Pathways (Wolff–Parkinson–White Syndrome) by Radiofrequency Current"; *N.E. Journal of Med., vol. 324, No. 23, Jun. 6, 1991.*

Lesh, "Application of Ultrasound Imaging to Catheter Ablation of Cardioac Arrthythmias"; *Biochemical Business International*; (date unknown).

McMath, "Percutaneous Laser Balloon Coagulation of Accessory Pathways"; *SPIE*, vol. 1425, pp. 165–169; 1991.

Schuger et al., "Long–Term Effects of Percutaneous Laser Balloon Ablation from the Canine Coronary Sinus"; pp. 947–954; May 18, 1992.

Schuger et al., "Percutaneous Transcatheter Laser Balloon Ablation for the Canine Coronary Sinus; Implications for the Wolff–Parkinson–White Syndrome", *Lasers In Surgery and Medicine*, vol. 10, No. 2, 1990.

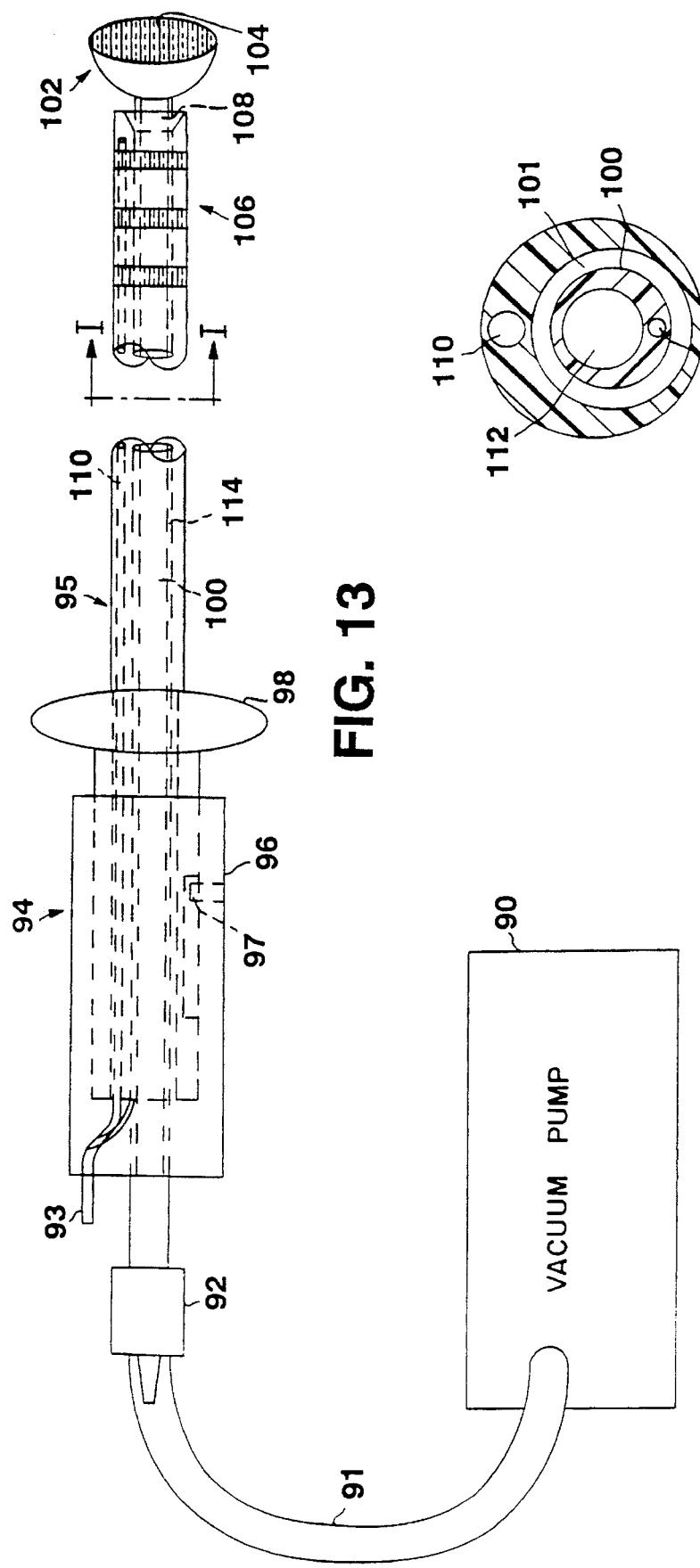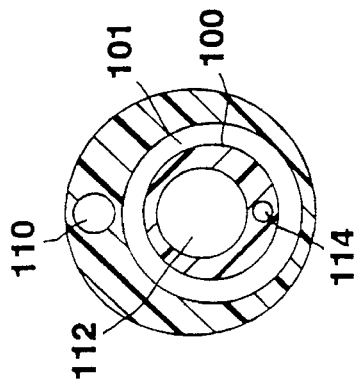

5,575,772

ALBATION CATHETERS

This is a continuation of application Ser. No. 08/086,740, filed Jul. 1, 1993, now abandoned.

BACKGROUND OF THE INVENTION

This invention relates to ablation catheters, particularly for use in ablating tissue in the chambers of a patient's heart.

The disorders that can be treated by ablating cardiac tissue include general arrhythmias, ventricular tachycardia, atrial fibrillation, atrial flutter, and Wolff-Parkinson-White Syndrome (WPW). Typically, ventricular tachycardia and WPW are treated by RF coagulation or DC discharge applied to cardiac tissue by electrode-tipped, deformable, and preset curved catheters. These catheters are of similar construction to those used in the art for electrically mapping the heart.

In order to navigate through the patient's vascular system, cardiac catheters are limited to small diameters. A typical mapping or ablation catheter has small electrodes mounted on the distal end of the catheter shaft. The electrodes can be arranged in bipolar pairs at the distal end of a catheter to ablate tissue by passing RF or DC electrical current between them through the surrounding myocardium. Alternatively, a single electrode could be disposed at the distal tip of a catheter, the single electrode being used to cause RF or DC electrical energy to pass directly through the heart tissue to a grounding plate on the surface of the patient's body.

Typically, the area of cardiac tissue that must be ablated is several times the size of the ablation region of the small electrode ablation catheters. Thus, a carpet bombing approach (i.e., ablating at many discrete sites) can be used to successfully treat cardiac disorders. This technique can lead to nonuniform ablation, as well as incomplete ablation if the ablation electrodes are not always directly in contact with myocardial tissue at each discrete site.

It is known to use a suction hole at a distal end of a catheter to engage tissue and thereby to hold the catheter in a fixed location in a patient's body while a distal ring electrode is placed in contact with tissue.

An alternative method for treating disorders in the heart is described in co-pending U.S. application Ser. No. 07/957,533, filed Oct. 5, 1992 by Daniel Bruce Fram et al., the entire disclosure of which is hereby incorporated herein in its entirety. As described in this co-pending application, a catheter having a balloon mounted on its distal end is inserted into the coronary sinus or great cardiac vein. The balloon is inflated with fluid within the coronary sinus and is heated by a heating device located within the balloon. Tissue surrounding the coronary sinus is ablated by thermal conduction from the fluid to the tissue through the wall of the balloon.

SUMMARY OF THE INVENTION

In one aspect, the invention features a method of ablating heart tissue within a body of a living being. A balloon catheter is provided that includes a catheter shaft constructed for insertion into a blood vessel, an inflatable balloon mounted on a distal portion of the catheter shaft, and a heating device mounted on the distal portion of the catheter and arranged for heating tissue in contact with the balloon while the balloon is inflated. The catheter shaft and the balloon are sized and constructed to permit the distal portion of the catheter shaft to be inserted into an atrium or ventricle of a heart while the balloon is deflated. The distal portion of the catheter is positioned within the atrium or ventricle and adjacent to a wall of the atrium or ventricle. The balloon is inflated with fluid while the balloon is within the atrium or ventricle, and while the balloon is inflated it is engaged in direct contact with a wall of the atrium or ventricle. Tissue surrounding the balloon is heated through use of the heating device while the balloon is inflated.

The invention provides a large area of ablation in an atrium or ventricle of the heart, through direct contact of a relatively large ablation device with a wall of an atrium or ventricle. The balloon is preferably sufficiently deformable under stress to conform to the irregular shape of the various chambers of the heart. The deformability of the balloon also allows for a uniform ablation of cardiac tissue. In addition, the area of ablation can be controlled relatively easily by adjusting the pressure inside the balloon, thereby thereby adjusting the length of the balloon.

Another aspect of the invention features a cardiac ablation catheter constructed for insertion into a body of a living being. The cardiac ablation catheter includes a catheter shaft, an inflatable balloon mounted on a distal portion of the catheter shaft, a heating device mounted on the distal portion of the catheter shaft for heating tissue in contact with the balloon while the balloon is inflated, an electrode located on the distal portion of the catheter shaft, and a control circuit connected to the electrode and arranged to apply radio-frequency electrical current to the electrode for ablating tissue in contact with the electrode.

By combining together, in a single catheter, an ablation electrode at the distal tip of the catheter and a heated balloon, the invention provides for both discrete localized ablation of small areas of myocardium with the ablation electrode, as well as large area ablation with the heated balloon.

Another aspect of the invention features a cardiac ablation catheter that includes a catheter shaft constructed for insertion into a body of a living being, an inflatable balloon disposed annularly around a distal tip of the catheter shaft, a heating device mounted on a distal portion of the catheter shaft for heating tissue in contact with the balloon while the balloon is inflated, and an electrode located on the distal tip of the catheter for directly contacting tissue while the balloon is pressed against the tissue in an axial direction. The catheter shaft and balloon are sized and constructed to permit the distal portion of the catheter shaft to be inserted into the body while the balloon is deflated and to permit the balloon to be filled with a fluid inside the body.

The invention achieves the advantage of monitoring the ablation procedure with a single catheter by coupling the distal electrode to mapping circuitry. The distal electrode provides for sensing during ablation with the heated balloon, allowing for a highly controlled ablation procedure.

Another aspect of the invention features an ablation catheter that includes a catheter shaft constructed for insertion into a body of a living being and having a lumen extending longitudinally through it for coupling a proximal source of suction to a distal port located at the distal tip of the catheter, an electrode mounted on the distal portion of the catheter shaft, and a tissue-engagement device surrounding the distal port and constructed to engage tissue with suction when the port is placed adjacent to the tissue. The tissue-engagement device is constructed to cause the distal portion of the catheter shaft to be held in a fixed position relative to the tissue while the electrode is placed in contact with an internal body structure. In certain preferred embodiments, the electrode is mounted directly on the tissue-engagement device or is adjacent thereto.

By combining, on a single catheter, a tissue-engagement device with an ablation electrode, the invention reduces the likelihood of the electrode being moved from an identified ablation site, which could result in damage to normal tissue. In addition, the invention provides a means for assuring that the electrode remains in direct contact with the tissue to be ablated or mapped, especially if the electrode is mounted directly on the tissue-engagement device itself or adjacent thereto, thereby reducing the likelihood of insufficient ablation or poor mapping due to the electrode not being in contact with the tissue.

Numerous other features, objects and advantages of the invention will become apparent from the following detailed description when read in connection with the accompanying drawings.

DETAILED DESCRIPTION

We first briefly describe the drawings.

Drawings FIG. 1 is a side view of a catheter having a balloon mounted thereon.

FIG. 13 is a side view of a catheter having a suction cup at its distal end.

FIG. 14 is a sectional view of the catheter of FIG. 13 taken along line I—I in FIG. 13.

STRUCTURE AND OPERATION

Figure 1:
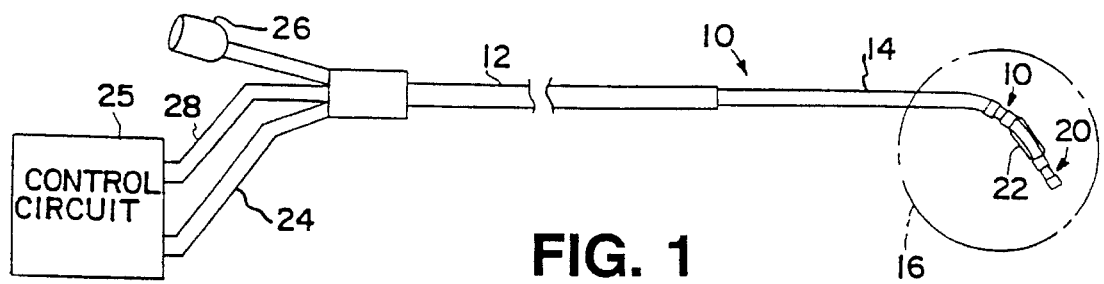
Figure 2:
FIG. 2 is an enlarged side view of a portion of the catheter shaft of FIG. 1.

FIG. 1 shows a heated balloon ablation catheter constructed for insertion into a heart and useful for ablating heart tissue containing abnormal electrical pathways, such as arrhythmogenic foci. The heated balloon ablation catheter comprises catheter shaft 10 having a proximal segment 12 and a distal segment 14. Proximal segment 12 includes an extruded wire 32 braided into catheter shaft 10 (see FIG. 2) for providing strength to the catheter while still maintaining the flexibility required to maneuver the catheter through a vascular system. Wire 32 is preferably made from stainless steel. Distal segment 14 comprises a flexible shaft material, preferably polyurethane, although other flexible biocompatible materials could be used. Catheter shaft 10 is constructed to have one-to-one torqueability.

In one embodiment, distal end 16 of catheter shaft 10 is capable of controlled deflection. A pull-wire (not shown) extends from a handle at the proximal end of the catheter through a lumen in catheter shaft 10 and is fastened to distal end 16 of catheter shaft 10. Distal segment 14 is constructed to be more flexible then proximal segment 12, so that when the handle is pulled back the pull wire causes distal end 16 to bend preferentially from an undeflected position to a deflected position.

Electrode pairs 18 and 20 are mounted on distal end 16 at either side of balloon 22, and are attached to conductors 49 (FIG. 3) that extend through the catheter shaft and that are connected to control circuit 25 by electrical connector 24. Control circuit 25 provides RF energy to the electrodes for ablating cardiac tissue, and also receives voltage potentials from the electrodes when the electrodes are used as electrophysiology mapping electrodes.

Balloon 22 is mounted circumferentially on distal end 16. Balloon 22 is elastic and preferably made from polyethylene cross-linked latex, although other biocompatible elastomer materials can be used. Balloon 22 is coupled to inflation port 26 through an inflation lumen extending along the length of catheter shaft 10. Balloon 22 is inflatable with fluid, preferably saline, which is injected by a syringe at balloon inflation port 26.

Figure 3:
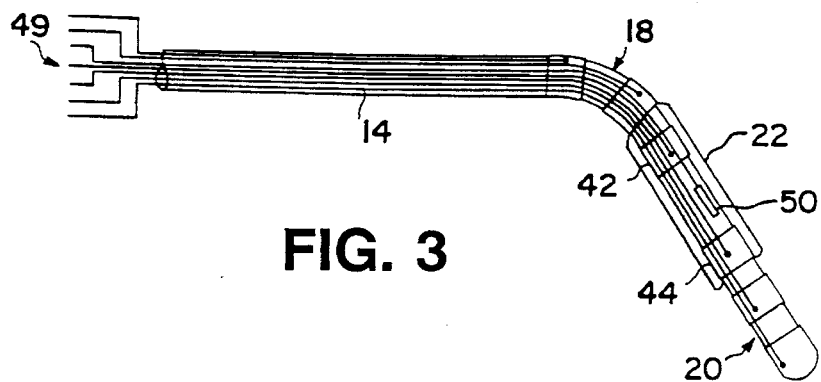
FIG. 3 is a side view of the distal end of the catheter of FIG. 1 with the balloon deflated.
Figure 4:
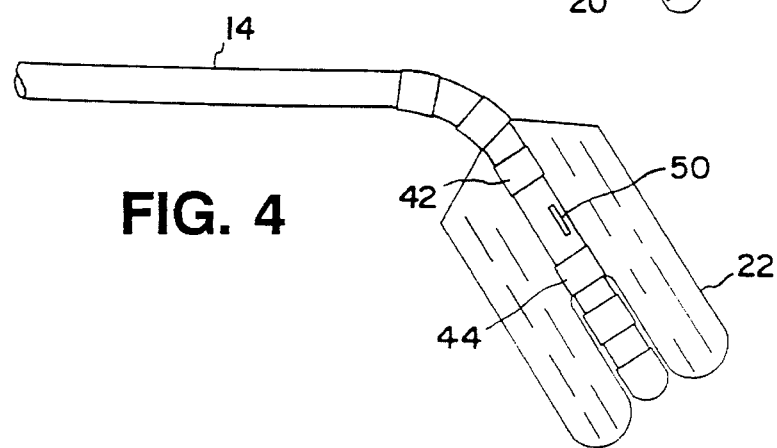
FIG. 4 is a side view of the distal end of the catheter of FIG. 1 with the balloon inflated.
Figure 5:
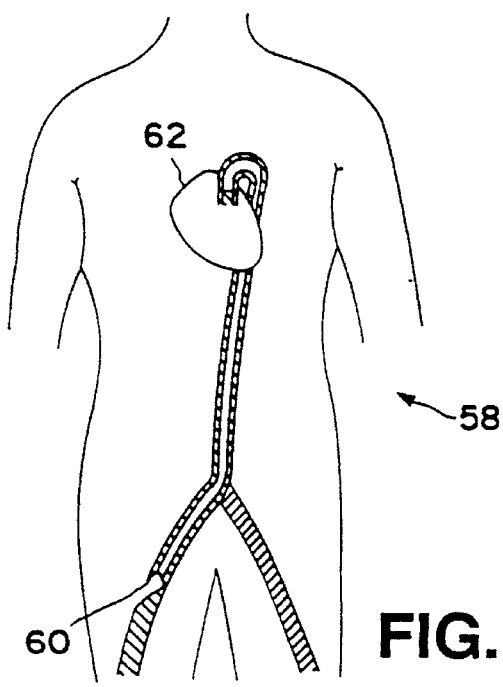
FIG. 5 is a pictorial representation of a human body illustrating a portion of the vascular system.

FIG. 3 shows a side view of distal end 16 with the balloon deflated, and FIG. 4 shows the balloon in its inflated condition. Electrodes 42 and 44 and thermistor 50 within the balloon are coupled to control circuit 25 by wires 49 through electrical connector 28. An RF current can be established between electrodes 42 and 44 for heating the fluid. Control circuit 25 receives signals from thermistor 50 representative of the temperature of the fluid and uses those signals to control the temperature of the fluid by controlling the amount of RF current passed between electrodes 42 and 44, in a manner described in detail in U.S. application Ser. No. 07/957,533, incorporated supra.

Figure 18:
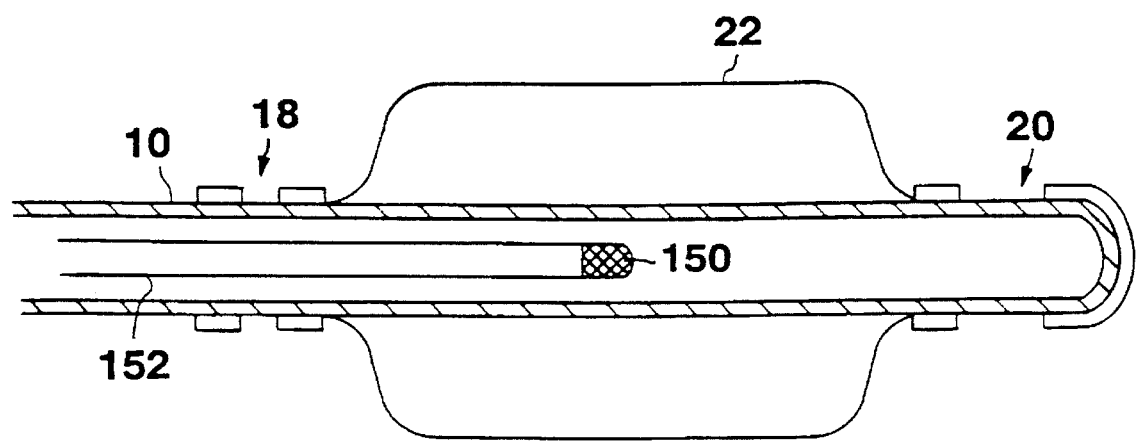
FIG. 18 is a sectional view of a catheter having an inflated balloon and electrodes mounted thereon and having an ultrasonic sensor for producing an ultrasonic image within a patient's body.

FIG. 18 shows a catheter having inflatable balloon 22 and electrodes 18 and 20, and further including an ultrasound transducer 150 mounted at the distal tip of a drive shaft 152 disposed inside catheter shaft 10. Ultrasound transducer 150 is used to produce ultrasound images from which the location of balloon 22 and electrodes 18 and 20 relative to heart tissue may be ascertained. The construction and operation of such an ultrasound transducer is described in detail in a U.S. patent application entitled "Catheters for Imaging, Sensing Electrical Potentials, and Ablating Tissue," by Robert J.

Crowley, filed on the same day as the present application, the entire disclosure of which is hereby incorporated in its entirety herein by reference. It is contemplated that each of the catheters described in the present application may be combined with such an ultrasound transducer and drive shaft.

Referring to FIGS. 5–9, there are shown pictorial representations of human body 58 illustrating a part of the vascular system. Distal section 16 of catheter shaft 10 is introduced into the vascular system of human body 58 through an opening in femoral vein 60. The catheter is shown entering the left side of the heart, but if the tissue to be ablated is located in the right atrium or ventricle, the catheter is inserted into the right side of the heart. Conventional fluoroscopic techniques can be used to navigate the catheter through the vascular system, if the catheter is provided with radiopaque markers or if a radiopaque contrast medium is used to inflate the balloon.

Figure 6:
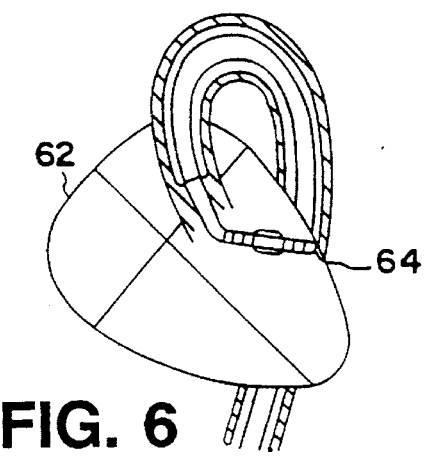
FIG. 6 is a pictorial representation of the catheter of FIG. 1 in the left ventricle with the balloon deflated and with the tip of the catheter in contact with heart tissue.

As shown in FIG. 6, distal tip 64 of the catheter shaft can be brought into contact with a wall of heart 62 by controllably deflecting the distal end of the catheter. The electrode senses electrical potentials within the heart for the purpose of locating cardiac tissue containing abnormal electrical pathways. Control circuit 25 (FIG. 1) can supply RF current to the electrode at distal tip 64 for ablation of localized cardiac tissue.

Figure 7:
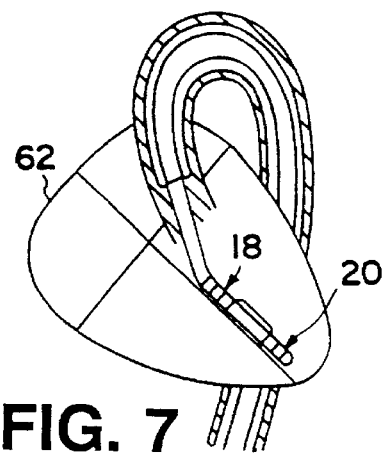
FIG. 7 is a pictorial representation of the catheter of FIG. 1 in the left ventricle with the balloon inflated and with the tip of the balloon in contact with heart tissue.

To ablate a larger area of cardiac tissue near distal tip 64, balloon 22 is inflated with fluid as shown in FIG. 7. The catheter maintains its position by virtue of its torsional rigidity. Alternatively, an ablation suction cup (described below in connection with FIG. 13) is included at the tip of the catheter shaft, the ablation suction cup being used to attach the catheter to the cardiac tissue. Balloon 22 conforms to the heart wall and thus allows a large area of cardiac tissue to be ablated.

When balloon 22 is used to ablate tissue, it is possible to monitor the progress of the ablation by sensing cardiac signals through the electrode located at distal tip 64. The sensed cardiac signals are used by control circuit 25 (FIG. 1) to regulate the RF energy supplied to the fluid inside balloon 22. For example, control circuit 25 can turn off the RF generation the instant the arrhythmogenic myocardium has been ablated to minimize damage to normal cardiac tissue.

Figure 8:
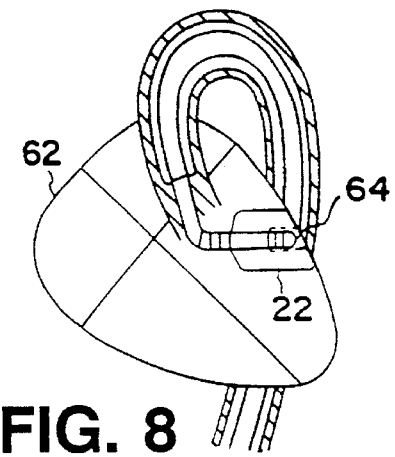
FIG. 8 is a pictorial representation of the catheter of FIG. 1 in the left ventricle with the balloon deflated and with the side of the balloon in contact with heart tissue.

As shown in FIG. 8, the distal end of the catheter can be positioned laterally against a heart wall. Cardiac tissue containing abnormal electrical pathways is located by mapping cardiac signals sensed through any of the electrodes. With balloon 22 deflated, localized myocardium can be ablated by passing RF current from control circuit 25 between bipolar electrode pairs 18 or 20.

Figure 9:
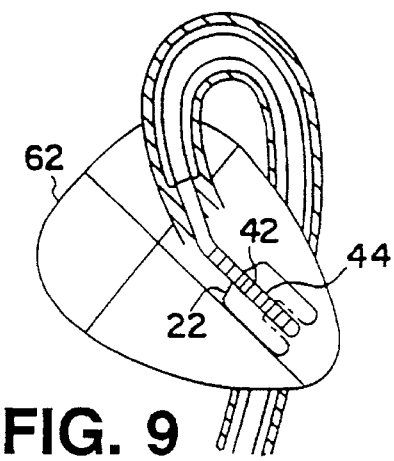
FIG. 9 is a pictorial representation of the catheter of FIG. 1 in the left ventricle with the balloon inflated and with the side of the balloon in contact with heart tissue.

Large areas of myocardium can be ablated by filling balloon 22 with fluid, as shown in FIG. 9. Balloon 22 conforms uniformly to the cardiac tissue over a large area of myocardium. The fluid is heated by passing an RF current between electrodes 42 and 44, and heat is transferred between the fluid and the myocardium, through balloon 22, thereby ablating the myocardium.

Following the ablation, balloon 22 is deflated, as shown in FIG. 8. Electrode pairs 18 and 20 are then used to sense local cardiac electrical activity to determine whether the tissue has been sufficiently ablated. If necessary, the ablation procedure can be repeated.

Figure 10:
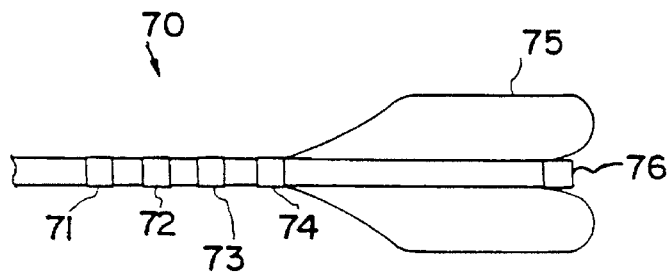
FIG. 10 is a side view of a catheter having an inflated balloon mounted at the distal end of the catheter shaft.
Figure 11:
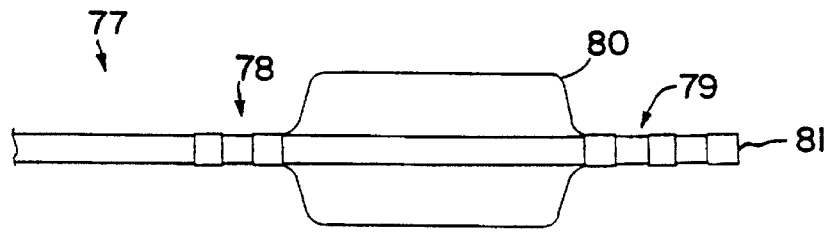
FIG. 11 is a side view of another catheter having an inflated balloon spaced from the distal end of the catheter shaft.
Figure 12:
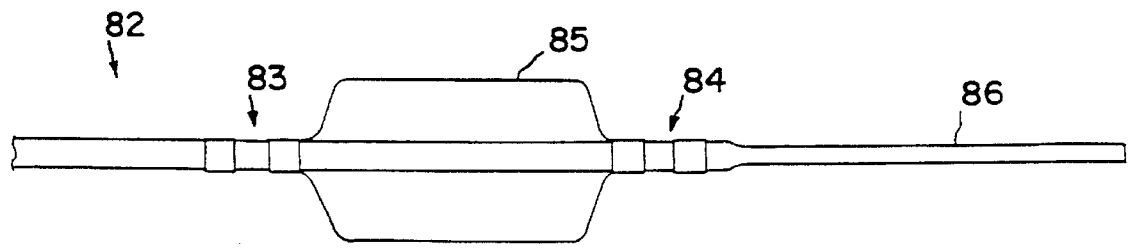
FIG. 12 is a side view of another catheter having an inflated balloon spaced from the distal end of the catheter shaft and having a distal extension for anchoring the distal end of the catheter in a fixed location.

FIG. 10, FIG. 11 and FIG. 12 illustrate different configurations of inflatable balloons and electrodes.

FIG. 10 shows distal end 70 of a catheter having electrodes 71, 72, 73 and 74 positioned on the proximal side of balloon 75. These electrodes are used primarily for mapping of cardiac tissue. However, it is also contemplated that bi-polar pairs of these electrodes may be used to ablate surrounding cardiac tissue. Electrode 76 is used for mapping tissue, as well as for electrophysiological sensing while balloon 75 is being used for ablation. Electrode 76 can also be used for monopolar ablation of tissue at select sites on the cardiac wall.

FIG. 11 shows distal end 77 of a catheter having two sets of bipolar electrodes pairs 78 and 79 mounted on either side of balloon 80. Electrode 81 is mounted on the tip of the catheter for providing additional mapping and/or ablation capability.

FIG. 12 shows a distal end 82 of another catheter, which is identical to the distal end of the catheter shown in FIG. 11 except for the elimination of electrode 81 and the addition of anchoring tip 72. Anchoring tip 72 is made of flexible material, preferably polyurethane, and is capable of controlled deflection in a manner similar to that described above.

Anchoring tip 72 can be positioned in various locations of the heart to stabilize balloon 22 at a desired position against a cardiac wall. For example, anchoring tip 72 can be extended into the coronary sinus while positioning balloon 22 against an atrial wall. Anchoring tip 72 can also be extended through a valve between chambers in the heart for providing additional stability.

FIG. 13 shows a suction catheter for ablating cardiac tissue. Rubber tube 91 couples vacuum pump 90 to vacuum port 92. Vacuum pump 90 can be any non-cycling pump (e.g., an electric pump). A peristaltic pump or other cycled pump should not be used because the vacuum provided would not be uniform.

Vacuum port 92 couples rubber tube 91 to vacuum lumen 112 (see FIG. 14), which extends the entire length of catheter shaft 95. The outside diameter of catheter shaft 95 is approximately eight to ten french, and its length is between one hundred to one hundred-twenty centimeters. Electrical connector 93 couples wires extending through mapping lumen 110 to an external monitoring apparatus and also couples wires extending through lumen 114 to an RF generator.

Retractable handle 94 includes base 96 coupled to catheter shaft 95 and grip 98 slidably mounted on catheter shaft 95 and coupled to retractable shaft 100. Retractable handle 94 has an open position, as shown in FIG. 13, and a closed position, which is obtained by moving grip 98 proximally and engaging it against base 96. Lock 97 restrains retractable handle 94 in either its open or closed position.

Figure 17:
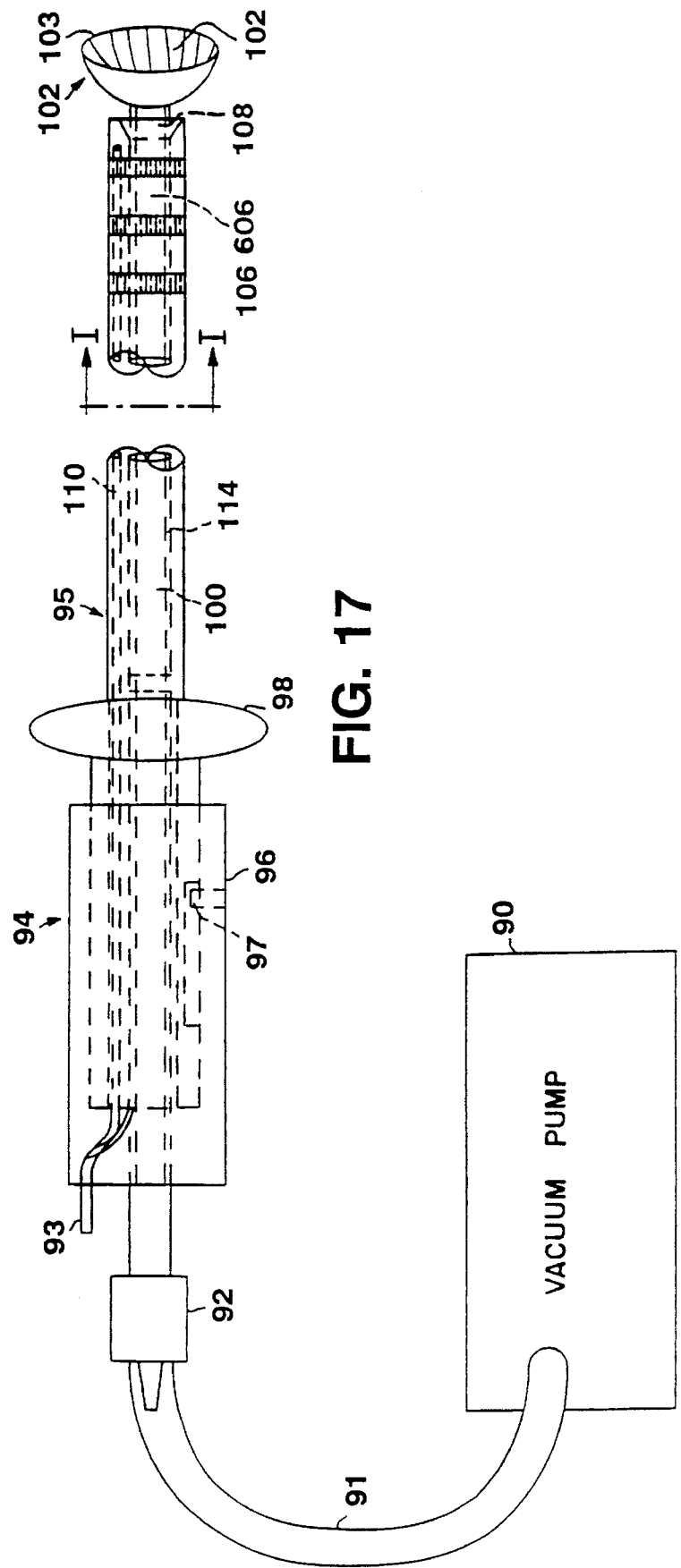
FIG. 17 is a side view of a catheter having a suction cup at its distal end.

Suction cup 102 is coupled to the distal end of retractable shaft 100 and is drawn into cavity 108 at the distal end of catheter shaft 95 by moving retractable handle 94 into its closed position. Suction cup 102 comprises a flexible polymer cup and an ablation electrode 104 lining the inner portion of the polymer cup. Ablation electrode 104 is made of conductive foil as shown in FIG. 13. Alternatively, ablation electrode 104 is made of a series of longitudinally disposed wires extending from the base of suction cup 102 to the outer rim as shown in FIG. 17. Wires extending through lumen 114 couple electrical connector 93 and ablation electrode 104.

It is contemplated that the suction cup feature of the catheter shown in FIG. 13 may be combined with any of the heated balloon electrophysiology catheters described above (substituting the suction cup of FIG. 13 for the distal electrode or distal anchoring extension shown in certain of the drawings).

Referring to FIG. 14, there is shown a sectional view of the suction catheter of FIG. 13, taken along the line I—I in FIG. 14. Conductors extending through mapping lumen 110 couple ring electrodes 106 and electrical port 93. Lumen 114 extends through retractable shaft 100, which is slidably mounted in lumen 101. Conductors disposed in vacuum lumen 112 extend through retractable shaft 100 and couple the electrode on suction cup 102 with an electrical connector at vacuum port 92.

The suction catheter is typically used to ablate tissue in the heart. The distal end of catheter shaft 95 enters the desired chamber of the heart and, local cardiac signals are sensed using ring electrodes 106 which are coupled to electrical connector 93 by conductors extending through mapping lumen 110. Electrodes other than ring electrodes may be used, such as orthogonal electrodes.

Once ring electrodes 106 have located cardiac tissue containing an abnormal electrical pathway, retractable handle 94 is moved into the open position, thereby releasing suction cup 102 from cavity 108. Ablation electrode 104 is then positioned against the tissue, and vacuum pump 90 is turned on. The established vacuum between suction cup 102 and the abnormal tissue causes ablation electrode 104 to be brought into intimate contact with the heart wall. The area of contact between the electrode-lined inner portion of suction cup 102 and the heart wall can be several times larger than the area of contact between a typical tip electrode 70 (see FIG. 10) and a heart wall, thereby allowing a larger area of tissue to be ablated. Once the suction cup is attached to the abnormal tissue, an RF generator coupled to electrical connector 93 causes an RF ablation current to pass between ablation electrode 104 and the cardiac tissue in a monopolar configuration.

Figures 15, 16:
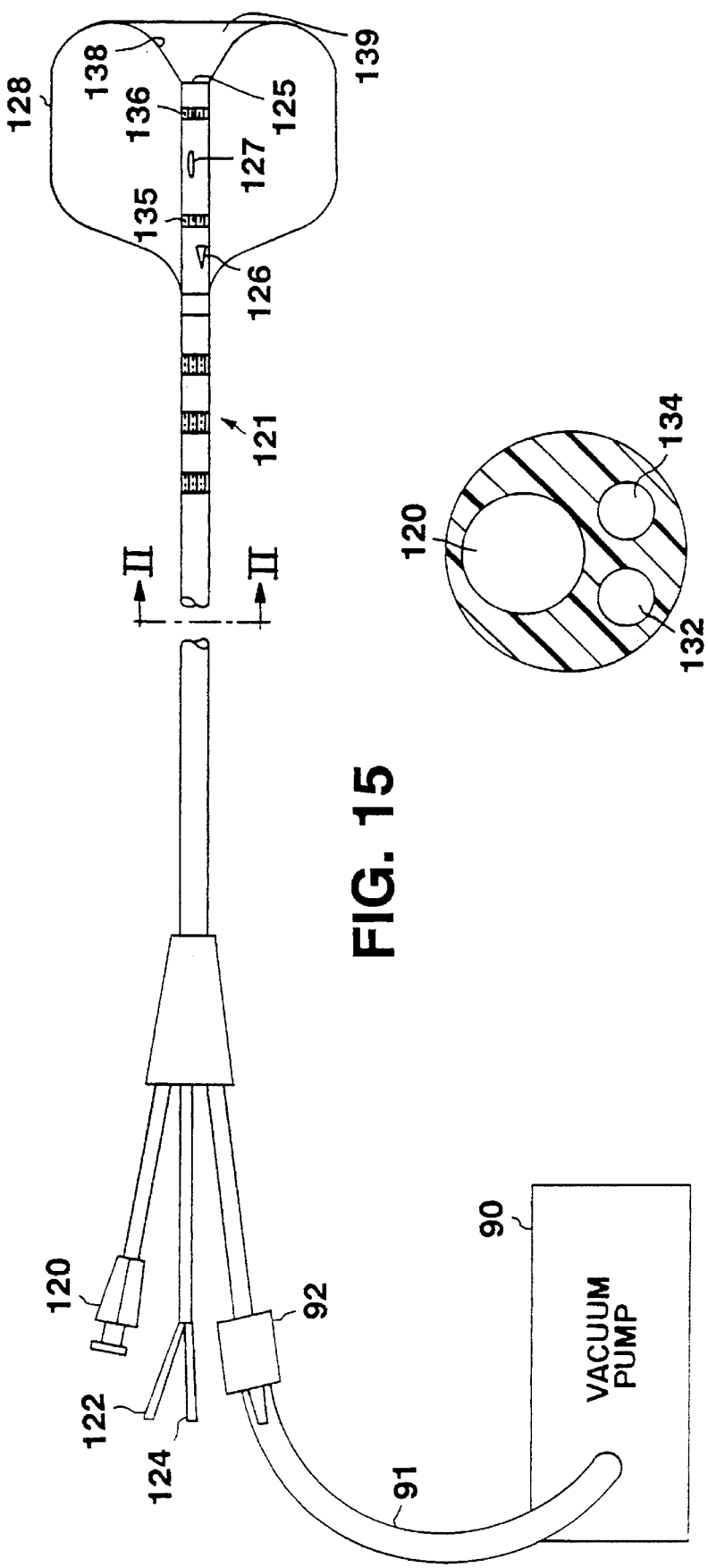
FIG. 15 is a side view of a catheter having an inflated balloon at its distal end that performs a suction anchoring function.
FIG. 16 is a sectional view of the catheter of FIG. 15 taken along line II—II in FIG. 15.

Referring to FIG. 15, there is shown a balloon suction ablation catheter. Rubber tube 91 couples vacuum pump 90 and vacuum port 92. Vacuum lumen 130 (FIG. 16) extends the length of the balloon suction ablation catheter and couples vacuum port 92 and distal lumen 125.

Electrical port 124 couples an RF generator to electrodes 135 and 136 inside balloon 128 via conductors that extend the entire length of the catheter through wire lumen 134. Additional conductors disposed in wire lumen 134 couple ring electrodes 121 to electrical connector 122, which is further coupled to a monitor. Inflation port 120, which is constructed to engage a syringe, is coupled to vacuum port 126 inside balloon 128 by inflation lumen 132.

In use of the device, ring electrodes 121 identify abnormal cardiac tissue to be ablated. Fluid, preferably saline, is injected by means of a syringe into inflation lumen 132 to inflate balloon 128 to a desired pressure, which is measured by a pressure gauge.

As shown in FIG. 15, balloon 128 is constructed such that when inflated the distal portion of balloon 128 forms horn cavity 138. Balloon 128, being compliant, allows horn cavity 138 to function as a suction cup. The distal portion of balloon 128 is placed against the cardiac tissue to be ablated and vacuum pump 90 is turned on. The vacuum established between balloon 128 and the tissue causes the balloon suction ablation catheter to become attached to the tissue. An RF current is then established between electrodes 135 and 136, which heats the fluid in balloon 128.

Alternatively, an annular electrode 139, which is coupled to RF port 124 via conductors extending through wire lumen 134, can be used to ablate cardiac tissue. Annular electrode 139 comprises conductive material (e.g., silver or gold) deposited on the surface of horn cavity 138. Alternatively, an annular electrode may be mounted on the distal tip of the catheter shaft immediately surrounding the suction port and immediately adjacent to the balloon.

The temperature inside balloon 128 is monitored by thermistor 127 coupled to electrical port 122 by conductors extending through wire lumen 134. The signal from thermistor 127 can then be used in a feedback circuit for controlling the current delivered by the RF generator for optimizing the ablation of the tissue and to minimize damage to normal tissue.

FIG. 16 is a sectional view of the catheter in FIG. 15 along line II—II showing three lumens disposed therein: vacuum lumen 130, inflation lumen 132 and wire lumen 134.

Other embodiments are within the following claims. For example, any of the inflatable balloons described above may be coated with a conductive material so that the balloon functions as a large, expandable electrode. Examples of such large, expandable electrodes are described in a U.S. patent application entitled "Heart Ablation Catheter with Expandable Electrode," by John E. Abele, filed on the same day as the present application, the entire disclosure of which is hereby incorporated in its entirety herein by reference.

What is claimed is:

1. A catheter device comprising:

a catheter shaft constructed for insertion into a body of a living being;

an inflatable balloon mounted on a distal portion of said catheter shaft, said catheter shaft and said balloon being sized and constructed to permit said distal portion of said catheter shaft to be inserted into said body while said balloon is deflated and to permit said balloon to be filled with a fluid inside said body;

a heating device mounted on said distal portion of said catheter shaft and constructed to cause a large area of tissue in contact with said balloon while said balloon is inflated to be heated;

an electrode, distinct from said heating device, located on a distal portion of said catheter device and configured to provide discrete localized ablation of small areas of tissue; and a control circuit connected to said electrode and arranged to apply radio-frequency electrical current to said electrode sufficient to enable said electrode to ablate tissue when said electrode is in contact with said tissue.

2. A catheter device in accordance with claim 1, wherein said catheter device is constructed to be introduced into a blood vessel, said distal portion of said catheter shaft is constructed to enter a heart chamber, and said inflatable balloon is constructed to engage a wall of said heart chamber.

3. A catheter device in accordance with claim 1, wherein said heating device is constructed to heat fluid within said balloon.

4. A catheter device in accordance with claim 1, further comprising a temperature feedback device mounted on said distal portion of said catheter shaft.

5. A catheter device in accordance with claim 1, wherein said balloon is disposed annularly around said catheter shaft and extends at least to the distal tip of said catheter shaft when said balloon is inflated to permit said balloon to be engaged against tissue in an axial direction.

6. A catheter device in accordance with claim 1, further comprising an anchoring device mounted on a distal portion of said catheter shaft and constructed to anchor said distal portion of said catheter shaft in a fixed location within said body.

7. A catheter device in accordance with claim 6, wherein:
said catheter shaft has a distal port and has a lumen extending longitudinally through said catheter shaft for coupling a proximal source of suction to said distal port; and
said anchoring device comprises a tissue-engagement device surrounding said distal port and constructed to engage tissue with suction when said port is placed adjacent to said tissue and suction is applied to said lumen.

8. A catheter device in accordance with claim 1, wherein said control circuit is configured to receive electrical potentials from said electrode when said electrode is used in an electrophysiology mapping mode.

9. A catheter device in accordance with claim 1, further comprising an ultrasound device located within said distal portion of said catheter shaft, said ultrasound device being arranged to direct ultrasound signals toward an internal structure within said body to produce an ultrasound image of said internal structure.

10. A catheter device in accordance with claim 1, wherein said balloon is disposed annularly around said catheter shaft is and spaced from the distal tip of said catheter shaft when said balloon is inflated.

11. A catheter device in accordance with claim 6, wherein said anchoring device comprises a distal extension of said catheter shaft extending distally beyond said balloon.

12. A catheter device, comprising:
a catheter shaft constructed for insertion into a body of a living being;
an inflatable balloon mounted on a distal portion of said catheter shaft, said catheter shaft and said balloon being sized and constructed to permit said distal portion of said catheter shaft to be inserted into said body while said balloon is deflated and to permit said balloon to be filled with a fluid inside said body, said balloon being disposed annularly around a distal tip of said catheter shaft and being constructed to extend beyond said distal tip and to be pressed against tissue in an axial direction when inflated;
a heating device mounted on said distal portion of said catheter shaft and constructed to cause tissue in contact with said balloon while said balloon is inflated to be heated; and
an electrode located on a distal tip of said catheter device, said electrode being positioned to be in direct contact with tissue while said balloon is pressed against said tissue in an axial direction.

13. A catheter device in accordance with claim 12, wherein said catheter device is constructed to be introduced into a blood vessel, said distal portion of said catheter shaft is constructed to enter a heart chamber, and said inflatable balloon is constructed to engage a wall of said heart chamber.

14. A catheter device in accordance with claim 12, wherein said heating device is constructed to heat fluid within said balloon.

15. A catheter device in accordance with claim 12, further comprising a temperature feedback device mounted on said distal portion of said catheter shaft.

16. A catheter device in accordance with claim 12, wherein said electrode is an ablation electrode.

17. A catheter device in accordance with claim 12, further comprising an anchoring device mounted on a distal portion of said catheter shaft and constructed to anchor said distal portion of said catheter shaft in a fixed location within said body.

18. A catheter device in accordance with claim 17, wherein:
said catheter shaft has a distal port and has a lumen extending longitudinally through said catheter shaft for coupling a proximal source of suction to said distal port; and
said anchoring device is said balloon, said balloon surrounding said distal port and being constructed to engage tissue with suction when said port is placed adjacent to said tissue and suction is applied to said lumen.

19. A catheter device in accordance with claim 12, wherein said electrode is mounted directly on said catheter shaft.

20. A catheter device in accordance with claim 12, wherein said electrode is coated onto a distal end of said balloon.

21. A catheter device in accordance with claim 12, wherein said electrode is an electrophysiology sensing electrode.

22. A catheter device in accordance with claim 12, further comprising an ultrasound device located within said distal portion of said catheter shaft, said ultrasound device being arranged to direct ultrasound signals toward an internal structure within said body to produce an ultrasound image of said internal structure.

23. A catheter device in accordance with claim 17, wherein said anchoring device comprises a distal extension of said catheter shaft extending distally beyond said balloon.

24. A catheter device, comprising,
a catheter shaft constructed for insertion into a body of a living being, said catheter shaft having a distal port and having a lumen extending longitudinally through said catheter shaft for coupling a proximal source of suction to said distal port;
an electrode located on a distal portion of said catheter device;
a tissue-engagement device surrounding said distal port and constructed to engage tissue with suction when said port is placed adjacent to said tissue and suction is applied to said lumen, said tissue-engagement device being constructed to cause said distal portion of said catheter shaft to be held in a fixed position relative to said tissue while said electrode is placed in contact with an internal body structure to reduce likelihood of said electrode being moved from said ablation site.

25. A catheter device in accordance with claim 24, wherein said electrode is mounted directly on said tissue-engagement device.

26. A catheter device in accordance with claim 24, wherein said electrode is mounted on said catheter shaft, adjacent to said tissue-engagement device.

27. A catheter device in accordance with claim 24, wherein said catheter is constructed to be introduced into a blood vessel, said distal portion of said catheter shaft is constructed to enter a heart chamber, and said tissue-engagement device is constructed to engage a wall of said heart chamber.

28. A catheter device in accordance with claim 24, wherein said tissue-engagement device comprises an inflatable balloon disposed annularly around said distal portion of said catheter shaft.

29. A catheter device in accordance with claim 28, further comprising a heating device mounted on said distal portion of said catheter shaft and constructed for heating fluid within said balloon.

30. A catheter device in accordance with claim 24, wherein said tissue-engagement device is constructed to have an open, radially extending position and a closed, collapsed position.

31. A catheter device in accordance with claim 24, wherein said electrode is an ablation electrode.

32. A catheter device in accordance with claim 24, wherein:

said tissue-engagement device comprises a flexible material molded in the shape of a cup.

33. A catheter device in accordance with claim 30, wherein said catheter shaft comprises a cavity constructed to hold said tissue-engagement device when said tissue-engagement device is in said closed position.

34. A catheter device in accordance with claim 30, wherein said catheter shaft has a pull-wire lumen extending longitudinally through said catheter shaft, and said catheter shaft further comprises a retractable handle disposed at a proximal end of said catheter shaft, and a pull wire extending through said pull-wire lumen for coupling said retractable handle and said tissue engagement device, said retractable handle being constructed to retract said tissue-engagement device into said closed position and to advance said tissue-engagement device into said open position.

35. A catheter device in accordance with claim 24, wherein said electrode is an electrophysiology sensing electrode.

* * * * *